(12) United States Patent
Rousseau et al.

(10) Patent No.: US 8,371,308 B2
(45) Date of Patent: Feb. 12, 2013

(54) MAGNETIC IMPLANTS AND METHODS FOR TREATING AN OROPHARYNGEAL CONDITION

(75) Inventors: Robert A. Rousseau, Ottsville, PA (US); Kevin S. Weadock, Hillsborough, NJ (US); An-Amin Jason Sung, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 932 days.

(21) Appl. No.: 12/378,573

(22) Filed: Feb. 17, 2009

(65) Prior Publication Data
US 2010/0211184 A1 Aug. 19, 2010

(51) Int. Cl.
*A61F 5/56* (2006.01)
*A61B 19/00* (2006.01)

(52) U.S. Cl. .................. 128/848; 128/897; 602/902
(58) Field of Classification Search .............. 128/848, 128/897–899; 602/902; 600/12
See application file for complete search history.

(56) References Cited

U.S. PATENT DOCUMENTS

| | | | |
|---|---|---|---|
| 5,284,161 A | 2/1994 | Karell | |
| 5,483,077 A | 1/1996 | Glavish | |
| 5,792,067 A | 8/1998 | Karell | |
| 6,161,541 A | 12/2000 | Woodson | |
| 6,250,307 B1 | 6/2001 | Conrad et al. | |
| 6,638,284 B1 | 10/2003 | Rousseau et al. | |
| 6,755,868 B2 | 6/2004 | Rousseau | |
| 6,800,082 B2 | 10/2004 | Rousseau | |
| 6,955,172 B2 | 10/2005 | Nelson et al. | |
| 6,981,944 B2 | 1/2006 | Jamiolkowski et al. | |
| 7,017,582 B2 | 3/2006 | Metzger et al. | |
| 7,288,075 B2 | 10/2007 | Parihar et al. | |
| 7,297,102 B2 | 11/2007 | Smith et al. | |
| 2003/0004579 A1 | 1/2003 | Rousseau et al. | |
| 2005/0121039 A1* | 6/2005 | Brooks et al. ................. | 128/863 |
| 2005/0159637 A9* | 7/2005 | Nelson et al. .................. | 600/12 |
| 2006/0005843 A9* | 1/2006 | Nelson et al. ................. | 128/848 |
| 2006/0150986 A1 | 7/2006 | Roue et al. | |
| 2006/0207608 A1 | 9/2006 | Hirotsuka et al. | |
| 2006/0289015 A1* | 12/2006 | Boucher et al. ............... | 128/848 |

(Continued)

FOREIGN PATENT DOCUMENTS

| | | |
|---|---|---|
| WO | WO2004/021870 A2 | 3/2004 |
| WO | WO2005/046554 A2 | 5/2005 |

(Continued)

OTHER PUBLICATIONS

Notification of Transmittal of the International Search Report and the Written Opinion of the International Search Authority or the Declaration mailed on May 25, 2010 for PCT/US2010/023152; International Filing Date: Apr. 2, 2010.

(Continued)

*Primary Examiner* — Nicholas Lucchesi
*Assistant Examiner* — Kari Petrik

(57) ABSTRACT

Magnetic devices and implantation methods are provided for use in the treatment of obstructive sleep apnea. The devices include a sheet-like element having ferromagnetic qualities. The device may also include a permanent magnet attached to the sheet-like element by magnetic forces. The devices are implanted in soft tissue surrounding the airway and in tissue space beneath the pharyngeal wall to exert forces on and/or change the shape of the soft tissue. The magnetic devices may also include a bladder containing a magnetorheological fluid that stiffens soft tissue when exposed to a magnetic field.

11 Claims, 11 Drawing Sheets

U.S. PATENT DOCUMENTS

| | | | |
|---|---|---|---|
| 2007/0119463 A1 | 5/2007 | Nelson et al. | |
| 2007/0144531 A1 | 6/2007 | Tomas et al. | |
| 2007/0209665 A1 | 9/2007 | Gillis et al. | |
| 2007/0246052 A1 | 10/2007 | Hegde et al. | |
| 2007/0256693 A1 | 11/2007 | Paraschac et al. | |
| 2007/0272257 A1 | 11/2007 | Nelson et al. | |
| 2008/0035158 A1* | 2/2008 | Pflueger et al. | 128/848 |
| 2008/0199824 A1* | 8/2008 | Hargadon | 433/6 |
| 2010/0294284 A1* | 11/2010 | Hohenhorst et al. | 128/848 |
| 2011/0178439 A1* | 7/2011 | Irwin et al. | 600/590 |

FOREIGN PATENT DOCUMENTS

| | | |
|---|---|---|
| WO | WO 2009/036094 A2 | 3/2009 |

OTHER PUBLICATIONS

"Obstructive Sleep Apnea; Implications for Cardiac and Vascular Disease"; Shamsuzzaman, et al., JAMA, vol. 290; No. 14; pp. 1906-1914; Oct. 8, 2003.

"Effects of Electrical Stimulation to the Soft Palate on Snoring and Obstructive Sleep Apnea"; Schwartz, et al., Journal of Prosthetic Dentistry, pp. 273-281, Sep. 1996.

"First Results on Daytime Submandibular Electrostimulation of Suprahyoidal Muscles to Prevent Night-Time Hypopharyngeal Collapse in Obstructive Sleep Apnea Syndrome"; Wiltfang, et al.; International Journal of Oral & Maxillofacial Surgery; pp. 21-25 (1999).

"The Surgical Treatment of Snoring" Harries, et al.; Journal of Laryngology and Otology; pp. 1105-1106, Sep. 1996.

"Snoring: A Review and a Reassessment"; Cole, et al.; Journal of Otolaryngology; pp. 303-306 (1995).

"Biomechanics of Snoring"; Huang, et al.,; Endeavour Science, vol. 19 (3): pp. 96-100 (1995).

"Upper Airway and Soft Tissue Changes Induced by CPAP in Normal Subjects"; Am. J. Respir. Crit. Care Med.; vol. 154, No. 4, pp. 1106-1116, Oct. 1996.

* cited by examiner

MAGNETIC IMPLANTS AND METHODS FOR TREATING AN OROPHARYNGEAL CONDITION

FIELD OF THE INVENTION

The present invention relates generally to the surgical treatment of oropharyngeal conditions such as obstructive sleep apnea and snoring, and more particularly, to the use of magnetic implants to alter airway characteristics or to reduce airway obstruction.

BACKGROUND OF THE INVENTION

Sleep apnea and snoring are oropharyngeal conditions that are often related. Several forms of sleep apnea have been identified. Obstructive sleep apnea (OSA) is caused by a blockage of the airway, usually when the soft tissue in the throat collapses and closes during sleep. Less common forms of sleep apnea include central sleep apnea (CSA), wherein the airway is not blocked but the brain fails to signal the muscles to breathe, and mixed apnea which, as the name implies, is a combination of OSA and CSA.

As shown in FIG. 1A, an air passage 140a of a patient 101a is open while the patient is in the awake state. The soft tissue components, including the rear of the tongue, the soft palate and the pharyngeal walls 132a of the air passage are supported by the underlying musculature to maintain the passageway in the open condition. During an obstructive sleep apnea event, illustrated in FIG. 1B, the air passage 140b of a patient 101b is partially or completely blocked by surrounding soft tissue 132b, which has collapsed due to the relaxation of the supporting musculature and has been displaced during sleep by gravity or other forces.

With each apnea event, the brain briefly arouses the sleeping person in order to resume breathing, but sleep is consequently extremely fragmented and of poor quality. Untreated, sleep apnea can cause high blood pressure, cardiovascular disease, memory problems, weight gain, impotency, and headaches. Moreover, untreated sleep apnea may be responsible for job impairment, motor vehicle crashes, and marital discord.

According to the National Institutes of Health, sleep apnea is very common, as common as adult diabetes, and affects more than twelve million Americans. The factors that increase the risk of having OSA include being male, overweight, and over the age of forty, but sleep apnea can strike anyone at any age, even children. Because of the lack of awareness by the public and healthcare professionals, the vast majority of patients remain undiagnosed and therefore untreated, despite the fact that this serious disorder can have significant consequences.

Attempts to provide an effective treatment for obstructive sleep apnea have yielded unsatisfactory results. For example, electrical stimulation of the soft palate has been suggested to treat snoring and obstructive sleep apnea. Such a teaching is found in Schwartz et al., "Effects of electrical stimulation to the soft palate on snoring and obstructive sleep apnea," J. Prosthetic Dentistry, pp. 273-281 (1996). Devices to apply electrical stimulation are described in U.S. Pat. Nos. 5,284,161 and 5,792,067. Electrical stimulation to treat sleep apnea is also discussed in Wiltfang et al., "First results on daytime submandibular electrostimulation of suprahyoidal muscles to prevent night-time hypopharyngeal collapse in obstructive sleep apnea syndrome," International Journal of Oral & Maxillofacial Surgery, pp. 21-25 (1999). Such devices are appliances requiring patient adherence to a regimen of use as well as subjecting the patient to discomfort during sleep and repeated arousals during deep sleep.

Continuous Positive Airway Pressure (CPAP) has recently been adopted as a useful, albeit cumbersome, means of preventing sleep apnea. CPAP delivers air into the airway through a specially designed nasal mask or pillows. The mask does not breathe for the patient; the flow of air creates enough pressure when the patient inhales to keep the airway open. In effect, a pneumatic splint is formed in the airway. CPAP is considered the most effective non-surgical treatment for the alleviation of snoring and obstructive sleep apnea. Compliance, however, is only 50%, as patients complain about discomfort from the mask, hoses, etc. and that the equipment requires maintenance. Additionally, patients complain of discomfort such as bloating, nasal drying, and dry eyes.

Surgical treatments have also been employed. One such treatment is uvulopalatopharyngoplasty (UPPP). UPPP is discussed, for example, in Harries et al., "The surgical treatment of snoring," Journal of Laryngology and Otology, pp. 1105-1106 (1996), which describes removal of up to 1.5 cm of the soft palate. The use of UPPP in the treatment of snoring is assessed in Cole et al., "Snoring: A review and a Reassessment," Journal of Otolaryngology, pp. 303-306 (1995). In that procedure, about 2 cm of the trailing edge of the soft palate is removed through the use of a scalpel, laser or other surgical instrument, thereby reducing the tendency of the soft palate to flutter between the tongue and the pharyngeal wall of the throat. The procedure is frequently effective to alleviate snoring but has demonstrated limited effectiveness in moderate or severe apnea. The procedure is painful and frequently results in undesirable side effects. In particular, the reduction of the soft palate compromises the ability of the soft palate to seal off nasal passages during swallowing and speech. In an estimated 25% of uvulopalatopharyngoplasty patients, fluid escapes from the mouth into the nose while drinking.

Uvulopalatopharyngoplasty (UPPP) may involve lasting discomfort. For example, scar tissue on the soft palate may present a continuing irritant to the patient. In addition, UPPP is not reversible and may induce adverse side effects not justified by the benefits of the surgery. Furthermore, UPPP is targeted to the correction of deficiencies associated with the palate only and does not address issues associated with the collapse of the tongue and lateral pharyngeal walls.

Radiofrequency ablation of the soft palate, or Somnoplasty$^{SM}$, is similar in concept to the Laser Assisted Uvulopalatopharyngoplasty (LAUP), although a different energy source is used, and thermal lesions are produced within the tissues, rather than using a laser to ablate the tissue surface. For that reason, radiofrequency ablation appears to be growing in popularity as an alternative to LAUP. The Soinoplastysm device is approved by the U.S. Food and Drug Administration (FDA) for radiofrequency ablation of palatal tissues for simple snoring and radiofrequency ablation of the base of the tongue for OSA. In some situations, radiofrequency ablation of the soft palate and base of tongue are performed together as a multi-level procedure. To date, the treatments alone or in combination have failed to provide relief to more than 50% of patients.

Another device intended to treat snoring or obstructive sleep apnea is comprised of several braided PET cylinders that are implanted to make the tissues of the tongue or uvula more rigid and less prone to deflection against the pharyngeal wall. The Pillar™ Palatal Implant System, marketed by Restore Medical of St Paul, Minn., is an implantable device that has been cleared by the FDA 510(k) process. The device is a cylindrical-shaped segment of braided polyester filaments that is permanently implanted submucosally in the soft palate. The labeled indication of the device is as follows: "The Pillar™ Palatal Implant System is intended for the reduction of the incidence of airway obstructions in patients suffering from mild to moderate OSA (obstructive sleep apnea)." The device has been associated with a number of adverse side effects, including extrusion, infection, and patient discomfort.

The Repose™ device, marketed by Influent Medical LLC of Concord, N.H., involves the use of a titanium screw that is inserted into the posterior aspect of the mandible at the floor of the mouth. A loop of suture is passed through the tongue base and attached to the mandibular bone screw. The Repose™ procedure achieves a suspension or hammock of the tongue base making it less likely for the base of the tongue to collapse against the posterior pharyngeal wall during sleep. The reported duration of beneficial effects afforded by the implant is less than a year. Due to the high activity of the tongue during wakefulness, the suture component of this device has been shown in some cases to act as a "cheese cutter" to the tongue, causing device failure and requiring subsequent removal.

Magnets have also been considered as implants for the treatment of obstructive sleep apnea. These devices are currently being evaluated in clinical trials. Serious complications that can potentially occur with these implants include implant migration and flipping of the magnets, which can cause acute airway closure. Magnetic implants may also cause compression of tissue around the implant. U.S. Patent Application Serial No. 2007/0272257 to Nelson et al. discloses the use of carrier strip materials that encourage tissue ingrowth and hold the orientation of the magnets.

Nelson et al. also suggests the use of magnetorheological (MR) fluid composed of a soft ferromagnetic material suspended in an injectable media for treating pharyngeal collapse. The material may be injected into implanted compartments.

U.S. Patent Application Serial No. 2007/0246052 to Hedge et al. teaches the use of a deformable element constructed of an electroactive polymer. The element is inserted into tissue surrounding a patient's airway and is activated to stiffen that tissue, using induced current or a battery.

In summary, electrical stimulation of the musculature within the airway is ineffective since it arouses the patient from deep sleep. CPAP effectively manages OSA but has a very low patient compliance (less than 50% of patients continue the treatment). Surgical techniques and implants have also been evaluated, yet still do not provide a satisfactory and lasting solution. No one device seems capable of treating the multi-causal problem of obstructive sleep apnea. What is needed are methods and devices that reduce the burden of managing obstructive sleep apnea through a minimally invasive approach that provides long term and effective results. Ideally, the treatment should be adjustable and removable if necessary. The devices and methods described herein provide such treatments that offer long-term relief of OSA.

SUMMARY OF THE INVENTION

The present invention is directed to systems and methods for treating oropharyngeal conditions such as obstructive sleep apnea. One embodiment of the invention is an implantable device for treating obstructive sleep apnea. The device comprises a sheet-like element having features for allowing tissue ingrowth after implantation. The sheet-like element has a biocompatible outer surface, and comprises a ferromagnetic material.

The implantable device may further include a permanent magnet having a biocompatible outer surface, the permanent magnet being attached to the sheet-like element by a magnetic force between the permanent magnet and the sheet-like element.

Another embodiment of the invention is a method for surgically treating obstructive sleep apnea. The method comprises the steps of delivering an implantable device including a sheet-like element comprising a ferromagnetic material into a soft tissue component of a human air passage; permitting tissue ingrowth into tissue ingrowth features of the sheet-like element; and subjecting the implantable device to a magnetic field so as to exert a force on the soft tissue via the sheet-like element.

The method may additionally comprise the step of delivering a permanent magnet implant into tissue in a vicinity of the soft tissue component of the human air passage, whereby the permanent magnet implant creates the magnetic field. Alternatively, the permanent magnet may adapted to be used externally or in the mouth.

Another aspect of the invention is a method for surgically treating an oropharyngeal condition. The method comprises the steps of delivering a magnetorheological system comprising a magnetorheological fluid into a soft tissue component of an air passage; and delivering a permanent magnet to a location opposite the air passage from the soft tissue component; whereby a partial collapse of the air passage brings the permanent magnet and the magnetorheological fluid into proximity, thereby changing an apparent viscosity of the magnetorheological fluid.

Another embodiment of the invention is an implantable device for treating obstructive sleep apnea. The device comprises a sheet-like element having features for allowing tissue ingrowth after implantation, the sheet-like element having a biocompatible outer surface; a containment bladder attached to the sheet-like element; and a magnetorheological fluid contained within the bladder.

DETAILED DESCRIPTION OF THE INVENTION

The present invention is directed to devices and methods for use in treating obstructive sleep apnea. Techniques according to the invention subject an implanted device to a magnetic field that affects implant and changes characteristics of tissue surrounding an airway. Certain of the devices may be implanted in tissue surrounding the airway, while others may be worn by a patient as part of an appliance proximate that tissue. The devices are used in pairs, where at least one of the devices includes a magnet that subjects the other device to the magnetic field.

Figure 1A:
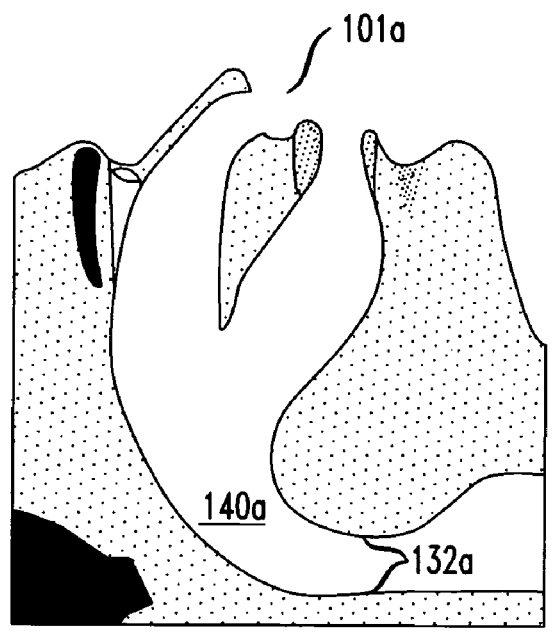
FIGS. 1A and 1B are schematic cross-sectional representations of a patient's upper airway.
Figure 1B:
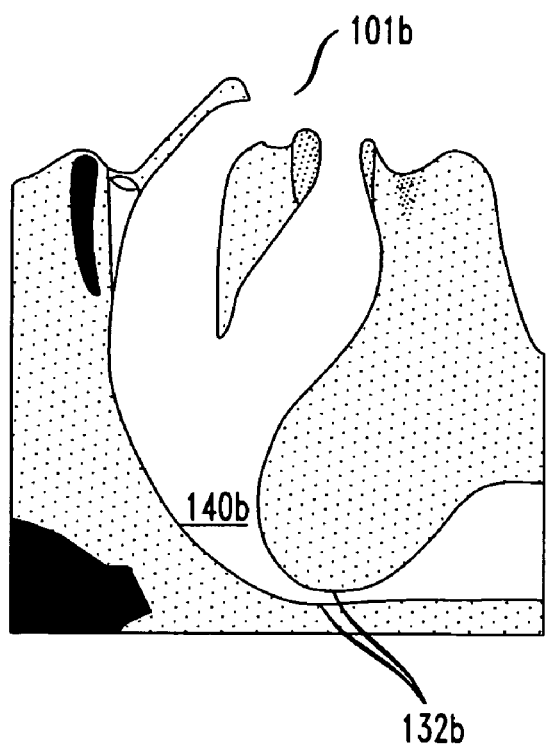
Figure 2:
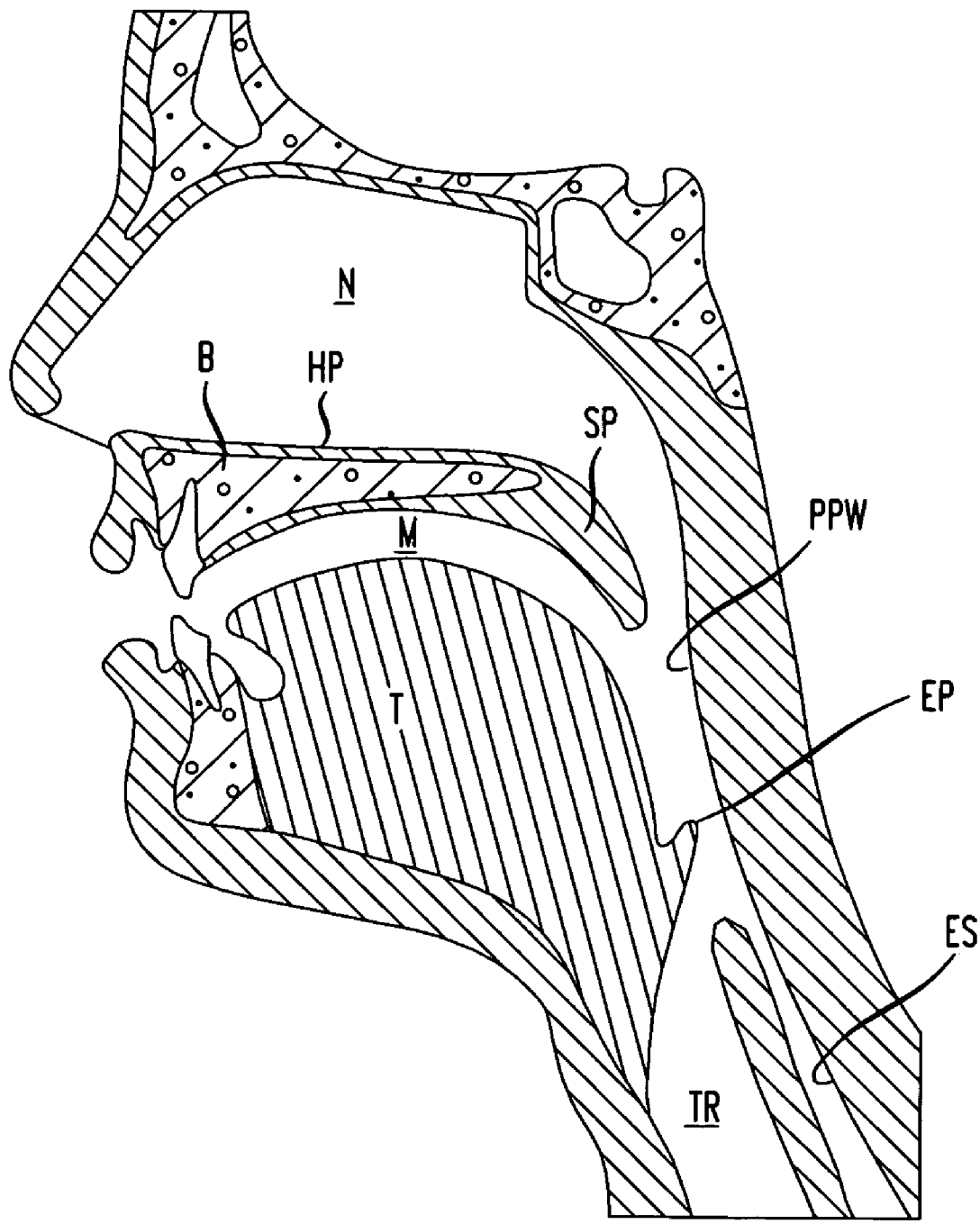
FIG. 2 is a schematic cross-sectional representation of a patient's upper airway.

FIG. 2 illustrates a cross-section of a patient's head with anatomical structures such as the nasal sinuses (N), bone (B) of the hard palate (HP), soft palate (SP), mouth (M), tongue (T), trachea (TR), epiglottis (EP), esophagus (ES) and posterior pharyngeal wall (PPW). The lateral pharyngeal walls (not shown in this illustration) are, as the name implies, lateral to the posterior pharyngeal wall. Certain of the implantable devices described herein may be positioned in any of the soft tissue structures surrounding the airway, including the pharyngeal walls, the soft palate and the tongue. Those devices, when subjected to a magnetic field, alter one or more characteristics of the surrounding soft tissue. The altered characteristics of those soft tissue structures maintain an airway for the patient, particularly when the diaphragm descends during inhalation and causes excessive negative pressure that might act to collapse the pharyngeal walls. The airway is maintained by exerting a force on soft tissue or stiffening a soft tissue structure to support it or to prevent it from collapsing.

Figure 3:
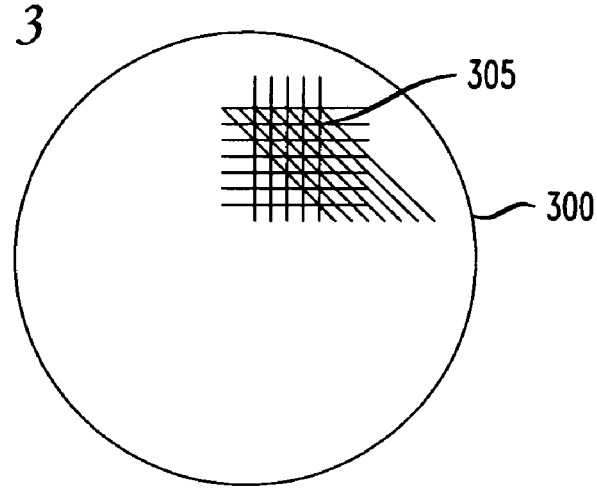
FIG. 3 is a schematic plan view of an implantable device in accordance with one embodiment of the invention.
Figure 3A:
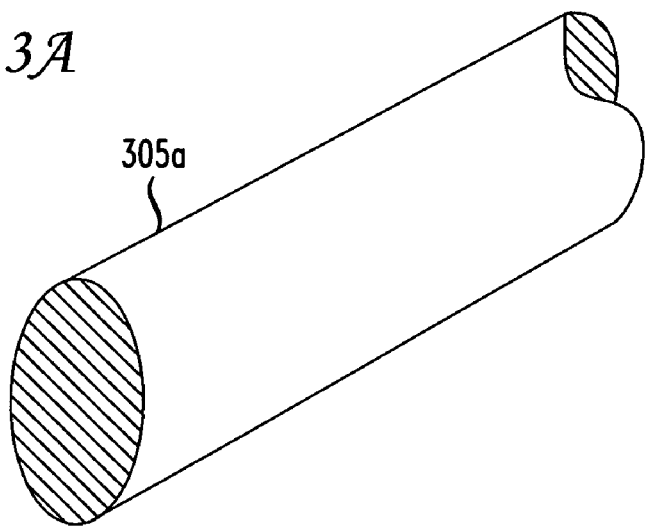
FIG. 3A is a schematic view of a filament used in constructing the implantable device of FIG. 3.

FIG. 3A is a plan view of a device 300 for implantation in soft tissue surrounding the airway of a patient. The device 300 is configured to promote and facilitate tissue ingrowth after the device is implanted, thereby stabilizing the implant in the surrounding tissue. The device 300 is also responsive to a magnetic field, exerting a force on the surrounding tissue when the device is subjected to the magnetic field.

The device 300 is a sheet-like element constructed from filaments or threads 305 that are woven, knitted, or are intermingled or bonded to form a medical textile or mesh. The device is constructed to frictionally or otherwise engage surrounding tissue upon implantation, and to thereby resist movement after placement within the tissue. The device 300 is biocompatible and is receptive to tissue ingrowth in the form of scar tissue that embeds during healing and becomes integrated with the device. That scar tissue reinforces the overall tissue mass in which the device is implanted. The element may encourage structural ingrowth of surrounding tissue, and may also encourage cellular ingrowth of tissue. Subsequent tissue engagement with the implantable device 300 and tissue ingrowth into the device serve to secure the device in the surrounding tissue, permitting the device to transmit forces to the surrounding tissue.

At least some of the filaments or threads 305 that comprise the sheet-like device 300 are ferromagnetic. Ferromagnetic materials exhibit a strong interaction such as an attractive force when in the presence of a magnet. Examples of ferromagnetic materials include iron, steel, cobalt, magnetite, various ferrites, manganese bismuth, manganese antimony, manganese arsenic, nickel, yttrium iron garnet, chromium (IV) oxide, gadolinium, dysprosium and europium oxide.

One example of a filament or thread 305a in accordance with the invention is shown greatly enlarged in FIG. 3A. The filament is formed of a biocompatible ferromagnetic material such as a martensitic (SAE 400 series) stainless steel. Other ferromagnetic materials may be used. The stainless steel is drawn to form filaments sufficiently fine to permit weaving, knitting, bonding or other processes to form a sheet-like element. Filament ends on the perimeter of the device may be backwoven or welded to reduce sharp edges. The sheet-like device 300 may be circular as shown, or may be formed in another shape to better conform to surrounding tissue. The resulting device 300 provides interstices between the filaments 305 to promote tissue ingrowth, enabling the device to exert a force on surrounding tissue when in the presence of a magnetic field.

Figure 3B:
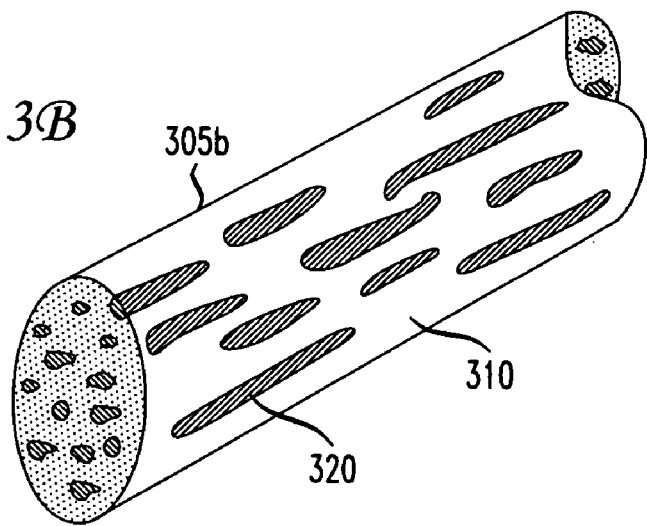
FIG. 3B is a schematic view of an alternative filament used in constructing the implantable device of FIG. 3.

Another filament 305b that may be used in the construction of the device 300 is shown in FIG. 3B. The filament 305b comprises a conglomerate of ferromagnetic particles 320 suspended in a matrix of non-magnetic biocompatible material 310. For example, martensitic stainless steel particles may be suspended in a polypropylene or other biocompatible polymer resin matrix to form the filament. The ferromagnetic particles 320 impart ferromagnetic qualities to the filament, causing the filament to exert a force in the presence of a magnetic field. Mechanical properties of the surrounding matrix provide flexibility that permits the use of various medical textile designs.

In one embodiment of the invention, the polymer resin matrix may be an absorbable material that is absorbed by the surrounding tissue over time, and replaced by scar tissue. The resulting structure after absorption is a matrix of scar tissue containing ferromagnetic particles. The particles exert forces on the surrounding tissue in the presence of a magnetic field.

Combinations of more than one type of filament may be used to construct the device 300. For example, ferromagnetic filaments such stainless steel filaments may be interwoven with non-magnetic polymer filaments. The resulting textile has magnetic properties while exhibiting favorable mechanical properties imparted by the polymer filaments.

Many medical textile designs are known to those skilled in the art of making mesh, fabrics, non-wovens, etc. for hernia repair. Medical textile products are based on fabrics, of which there are four types: woven, knitted, braided, and non-woven. The first three of these are made from yarns or filaments, whereas the fourth can be made directly from fibers, or even from polymers such as Gore-Tex®-based products or electrostatically spun materials from polyurethane. There is, therefore, a hierarchy of structure: the performance of the final textile product is affected by the properties of polymers whose structures are modified at between two and four different levels of organization.

Of the many different types of polymers, only a few can be made into useful fibers. This is because a polymer must meet certain requirements before it can be successfully and efficiently converted into a fibrous product. For example, the polymer chains should be linear, long, and flexible. Side groups of the polymers should be simple, small, or polar. Polymers should be dissolvable or meltable for extrusion. Chains should be capable of being oriented and crystallized.

Common fiber-forming polymers include cellulosics (linen, cotton, rayon, acetate), proteins (wool, silk), polyamides, polyester (PET), olefins, vinyls, acrylics, polytetrafluoroethylene (PTFE), polyphenylene sulfide (PPS), aramids (Kevlar, Nomex), and polyurethanes (Lycra, Pellethane, Biomer). Each of these materials is unique in chemical structure and potential properties. For example, among the polyurethanes is an elastomeric material with high elongation and elastic recovery, whose properties nearly match those of elastin tissue fibers. This material—when extruded into fiber, fibrillar, or fabric form—derives its high elongation and elasticity from alternating patterns of crystalline hard units and non-crystalline soft units.

Although several of the materials mentioned above are used in traditional textile as well as medical applications, various polymeric materials—both absorbable and non-absorbable—have been developed specifically for use in medical products.

The reactivity of tissues in contact with fibrous structures varies among materials and is governed by both chemical and physical characteristics. Absorbable materials typically excite greater tissue reaction, a result of the nature of the absorption process itself. Among the available materials, some are absorbed faster (e.g., polyglycolic acid, polyglactin acid) and others more slowly (e.g., polyglyconate). Semi absorbable materials such as cotton and silk generally cause less reaction, although the tissue response may continue for an extended time. Non-absorbable materials (e.g., nylon, polyester, polypropylene) tend to be inert and to provoke the least reaction. To minimize tissue reaction, the use of catalysts and additives is carefully controlled in medical-grade products.

As discussed, of the many types of polymers, only a few can be made into useful fibers that can then be converted into medical textile products. To make fibers, polymers are extruded by wet, dry, or melt spinning and then processed to obtain the desired texture, shape, and size. Through careful control of morphology, fibers can be manufactured with a range of mechanical properties. Tensile strength can vary from textile values (values needed for use in typical textile products such as apparel) of 2-6 g/d (gram/denier) up to industrial values (values typical of industrial products such as tire cords or belts) of 6-10 g/d. For high-performance applications, such as body armor or structural composites, novel spinning techniques can produce fibers with strengths approaching 30 g/d. Likewise, breaking extension can be varied over a broad range, from 10-40% for textile to 1-15% for industrial and 100-500% for elastomeric fibers.

Fibers or filaments are converted into yarns by twisting or entangling processes that improve strength, abrasion resistance, and handling. Yarn properties depend on those of the fibers or filaments as well as on the angle of twist. Yarns are interlaced into fabrics by various mechanical processes, including weaving, knitting, and braiding. There are three prevalent fabric structures used for medical implants or sutures: woven, in which two sets of yarns are interlaced at right angles; knitted, in which loops of yarn are intermeshed; and braided, in which three or more yarns cross one another in a diagonal pattern. Knitted fabrics can be either weft or warp knit, and braided products can include tubular structures, with or without a core, as well as ribbon.

There are also numerous medical uses for nonwoven fabrics (wipes, sponges, dressings, gowns), made directly from fibers that are needle-felted, hydroentangled, or bonded through a thermal, chemical, or adhesive process. Nonwovens may also be made directly from a polymer. Expanded polytetrafluoroethylene (ePTFE) products such as sutures and arterial grafts and electrostatically spun polyurethane used as tubular structures are examples of medical applications of polymer-to-fabric nonwovens.

The properties of fabrics depend on the characteristics of the constituent yarns or fibers and on the geometry of the formed structure. Whether a fabric is woven, knitted, braided, or nonwoven will affect its behavior. Fabrics that are woven are usually dimensionally very stable but less extensible and porous than the other structures. One disadvantage of wovens is their tendency to unravel at the edges when cut squarely or obliquely for implantation. However, the stitching technique known as a Leno weave—in which two warp threads twist around a weft—can substantially alleviate this fraying or unraveling.

Compared with woven fabrics, weft-knitted structures are highly extensible, but they are also dimensionally unstable unless additional yarns are used to interlock the loops and reduce the extension while increasing elastic recovery. Warp-knitted structures are extremely versatile, and can be engineered with a variety of mechanical properties matching those of woven fabrics. The major advantage of knitted materials is their flexibility and inherent ability to resist unraveling when cut. A potential limitation of knitted fabrics is their high porosity, which—unlike that of woven fabrics—cannot be reduced below a certain value determined by the construction. As a result, applications requiring very low porosity usually incorporate woven materials.

Typically employed in cords and sutures, braided structures can be designed using several different patterns, either with or without a core. Because the yarns crisscross each other, braided materials are usually porous and may imbibe fluids within the interstitial spaces between yarns or filaments. To reduce their capillarity, braided materials are often treated with a biodegradable (polylactic acid) or nonbiodegradable (Teflon®) coating. Such coatings also serve to reduce chatter or noise during body movement, improve hand or feel, and help position suture knots that must be transported by pressure from a surgeon's finger from outside the body to the wound itself.

The properties of nonwoven fabrics are determined by those of the constituent polymer or fiber and by the bonding process. For instance, expanded PTFE products can be formed to meet varying porosity requirements. Because of the expanded nature of their microstructure, these materials compress easily and then expand—a suture, for example, can expand to fill the needle hole made in a tissue—allowing for tissue ingrowth in applications such as arterial and patch grafts. Polyurethane-based nonwovens produce a product that resembles collagenous material in both structure and mechanical properties, particularly compliance (extension per unit pressure or stress). The porosity of both PTFE- and polyurethane-derived nonwovens can be effectively manipulated through control of the manufacturing processes.

In one embodiment of the invention, the device 300 is fabricated by warp knitting a monofilament polypropylene yarn that is approximately 3 to 6 mils in diameter. In one exemplary embodiment, the yarn is 3.5 mils in diameter. The monofilament yarn contains martensitic stainless steel particles having a diameter less than 1 mil. The particles may have an elongated shape and be oriented longitudinally in the monofilament during an extrusion manufacturing process. In this embodiment, the knitted mesh preferably has 40-80 courses per inch and 7-11 wales per inch. Other designs of medical textiles may also be used.

Figure 4:
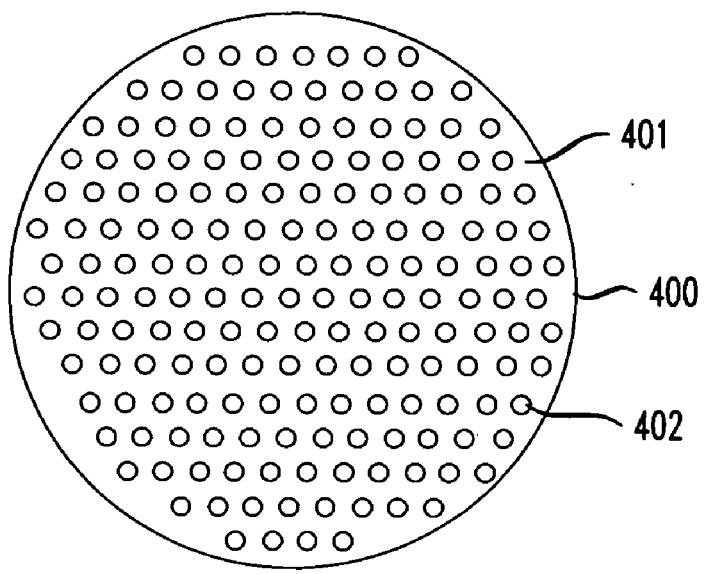
FIG. 4 is a schematic plan view of an implantable device in accordance with another embodiment of the invention.

The sheet-like element may alternatively be a perforated film or foil device 400, shown in FIG. 4. In that embodiment, a film 401 is perforated with a plurality of holes 402 to engage tissue and to allow tissue ingrowth. The size, shape and spacing of the holes may be optimized for those functions. Further, the size, shape and spacing of the holes 402 may be varied over the film 401 to promote greater tissue engagement in certain locations on the film. The film comprises a ferromagnetic material and exerts an attractive force when subjected to a magnetic field. To that end, the film or foil 401 is constructed from a ferromagnetic substance such as magnetic stainless steel or a polymer film containing ferromagnetic particles. The film or foil 401 is furthermore biocompatible, being constructed of biocompatible materials or being encapsulated in a biocompatible coating.

Figure 5:
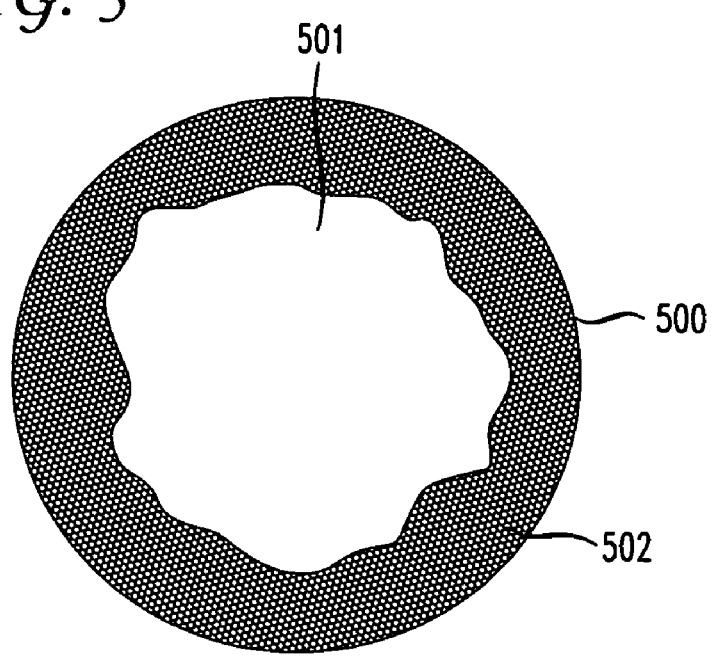
FIG. 5 is a schematic plan view of an implantable device in accordance with another embodiment of the invention.

Another embodiment of the device 500, shown in FIG. 5, comprises a sheet 501 having other types of tissue engaging features 502, alone or in combination with perforations. The features 502 may be restricted to a certain region of the device 500, such as the periphery as shown in FIG. 5, or may be distributed over the entire device. The features 502 may be corrugations, dimples, knurling or other embossed, molded or machined relief patterns that engage tissue in contact with the features. The features may include full or partial perforations with raised edges that engage surrounding tissue. The features 502 may alternatively be formed by a material or coating added to the sheet 501 to roughen the surface or otherwise provide features that promote or enhance tissue engagement and ingrowth.

Figure 6:
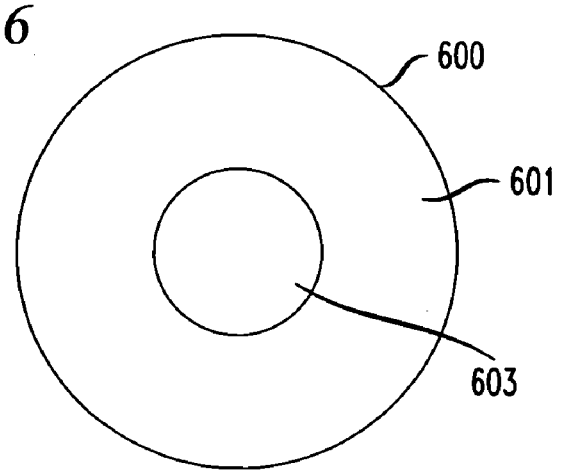
FIG. 6 is a schematic plan view of an implantable device including a magnet in accordance with another embodiment of the invention.

An implantable device 600 that includes a permanent magnet 603 according to the invention is shown in FIG. 6. The device includes a sheet-like element 601 that is ferromagnetic (i.e., exerts an attractive force when in the presence of a magnetic field), and a permanent magnet 603.

The sheet-like element 601 may be a medical textile that includes ferromagnetic filaments or filaments that contain ferromagnetic particles. Alternatively, the sheet may be a thin film formed of a ferromagnetic material or formed of a material containing ferromagnetic particles. In either case, the sheet-like element 601 also includes features for promoting tissue ingrowth, as described above. Those features may include the medical textile itself, or may include features formed in or on a film.

The device 600 additionally includes a permanent magnet 603. The magnet is preferably a rare earth magnet such as a neodymium magnet or a samarium-cobalt magnet. The permanent magnet 603 is coated with a non-absorbable biocompatible substance such as nylon, polyester or polypropylene. The permanent magnet 603 is attached to the sheet-like element 601 by the magnetic attractive forces between the permanent magnet 603 and the ferromagnetic materials contained in the sheet-like element 601. The magnet 603 is therefore removable from the sheet-like element 601 by simply overcoming the attractive forces between them. Because the magnet 603 and sheet-like element 601 are in close proximity, however, the attractive force between them maintains the attachment in use under attractive interactions with other magnets and ferromagnetic materials located some distance away, as described below.

Figure 6A:
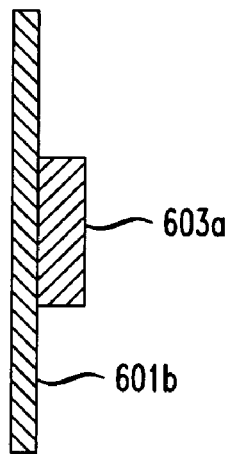
FIG. 6A is a schematic side view showing one embodiment of the implantable device of FIG. 6.

An example cross sectional geometry of the device 600 is shown in FIG. 6A. The magnet 603a is attached directly to the sheet-like element 601a at a planar interface. In use, the magnet may be attached to the sheet-like element at a location most suitable to the individual surgical application of the device, considering surrounding tissue condition, the direction of forces on the magnet and other factors.

Figure 6B:
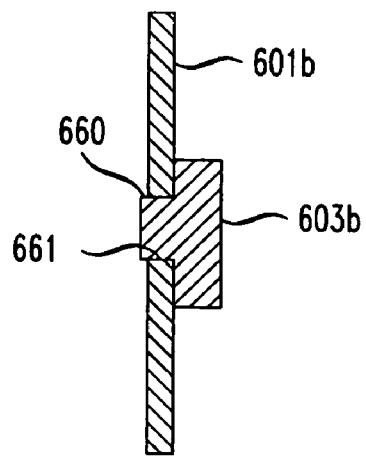
FIG. 6B is a schematic side view showing another embodiment of the implantable device of FIG. 6.

Another example cross sectional geometry of the device 600 is shown in FIG. 6B. At the interface of the magnet 603b with the sheet-like element 601b, locating elements fix the location of the magnet relative to the sheet like element. In the example shown, a shoulder 660 provided on the magnet 603b interfaces with a hole 661 in the sheet-like element 601b. The locating elements 660, 661 establish relative positions of the components when they are assembled, and prevent relative movement of those components in use, when they are subjected to magnetic forces that might otherwise cause sliding motion of the magnet on the sheet-like element.

Figure 7A:
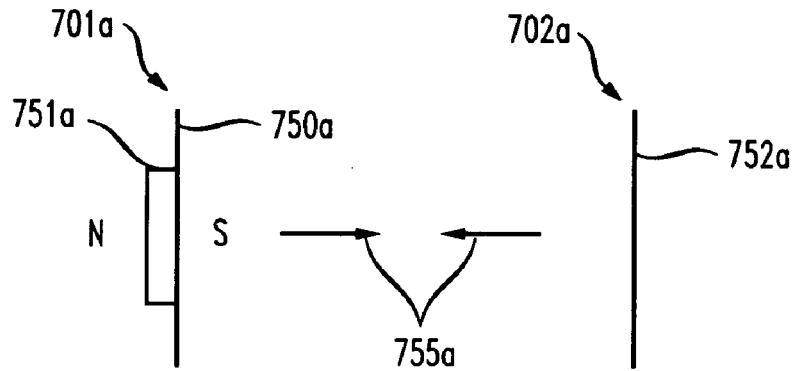
FIG. 7A is a schematic diagram showing one arrangement of the implantable devices of the invention.
Figure 7B:
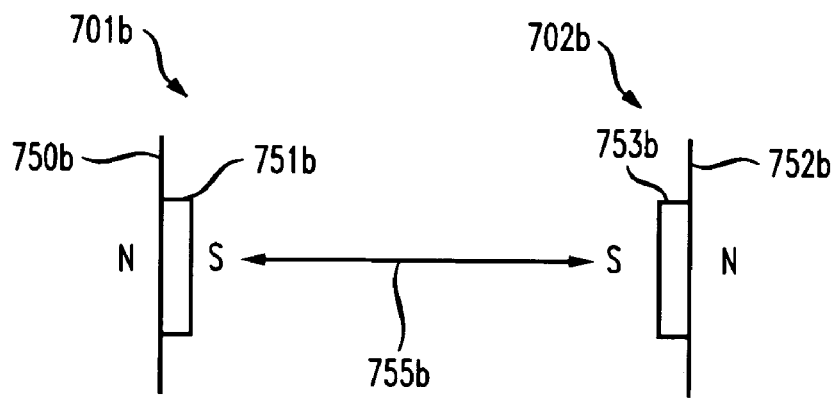
FIG. 7B is a schematic diagram showing another arrangement of the implantable devices of the invention.
Figure 7C:
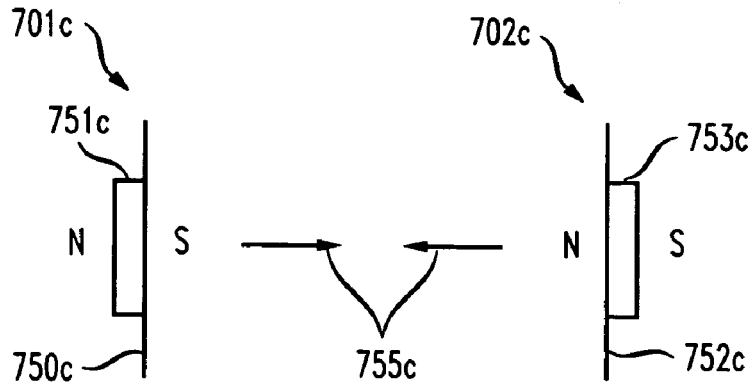
FIG. 7C is a schematic diagram showing another arrangement of the implantable devices of the invention.

The described implantable devices may be used in a variety of configurations in the treatment of obstructive sleep apnea. Several such configurations are shown in FIGS. 7A-7C. In one configuration, shown in FIG. 7A, a device 701a comprising a magnet 751a and a sheet-like element 750a is implanted in proximity with a device 702a comprising only a sheet-like element 752a. An attractive force 755a is created between the two implanted devices 701a, 702a by the attraction of the magnet 751a to the sheet-like element 752a. That attractive force is transmitted to surrounding tissue due to tissue ingrowth and engagement with the sheet-like elements 750a, 752a. While the magnet 751a is shown with its north pole facing away from the device 702a, the poles could be reversed without changing the effect.

The magnet 751a is shown attached to the sheet-like element 750a on a side of the sheet-like element opposite the device 702a. In that configuration, the attractive force 755a tends to strengthen the attachment between the magnet 751a and the sheet-like element 750a.

In some cases, such as where the distance from the magnet 751a to the device 702a must be minimized, it may be advantageous to attach the magnet to the sheet-like element 750a on a side closest to the device 702a. In that case, the magnetic force between the magnet 751a and the sheet-like element 750a, which stronger than the force 755a, keeps those two components attached.

In another configuration, shown in FIG. 7B, the devices 701b, 702b exert a repulsive force 755b on each other. Device 701b comprises a magnet 751b and a sheet-like element 750b, while the device 702b comprises a magnet 753b and a sheet-like element 752b. The magnets are attached to respective sheet-like elements by magnetic attraction between the magnets and sheet-like elements. The magnets 751b, 753b are arranged with like poles facing each other, resulting in a repulsive force 755b being transmitted through the sheet-like elements 750b, 752b to surrounding tissue. The magnets are shown attached to facing sides of the sheet-like elements 750b, 752b, resulting in increased attachment strength as well as a minimized distance between magnets.

A configuration shown in FIG. 7C shows two devices 701c, 702c exerting attractive forces 755c between them. Each device comprises a magnet 751c, 753c and a sheet-like element 750c, 752c. The use of two permanent magnets provides the configuration shown in FIG. 7C with a stronger attractive force than that of the configuration shown in FIG. 7A. The magnets are shown on sides of the sheet-like elements facing away from each other, thereby strengthening the attachment of the magnets to the sheet-like elements. The magnets may alternatively be attached on facing sides, decreasing magnet-to-magnet distance.

Optionally, image-enhancing substances such as radio-opaque or ultrasonically sensitive materials can be layered onto any of the surfaces of the implantable devices of the invention to aid in imaging of the device during and after deployment. In another embodiment, anti-microbial agents such as triclosan or antibiotics, or pain management medicaments are applied or coated to one or more surfaces of the components that comprise the device prior to deployment. Alternatively, the agents may be included in the polymers during the fabrication processes through extrusion, blending, casting, solvent mixing or other typical polymer processing means. The agents may be included within an absorbable component to provide controlled or profiled release of the substances during wound healing.

Orientation and configuration of the implantable devices in the patient may be selected depending on the particular patient anatomy. For example, a pair of opposing magnets as described with reference to FIG. 7B may be implanted in a patient as illustrated in a cross sectional view of the patient's lower head and neck shown in FIG. 8 and FIG. 9. In that embodiment, the devices 801, 802 are placed in opposing positions from each other across the patient's airway AW. The device 801 is placed behind the posterior pharyngeal wall PPW on the side that does not face the airway. For example, the device may be placed in a space beneath the pharyngeal wall formed during the implantation procedure, against the prevertebral fascia and musculature such as the longus capitus muscles. The device 802 is implanted in the tongue T.

Figure 8:
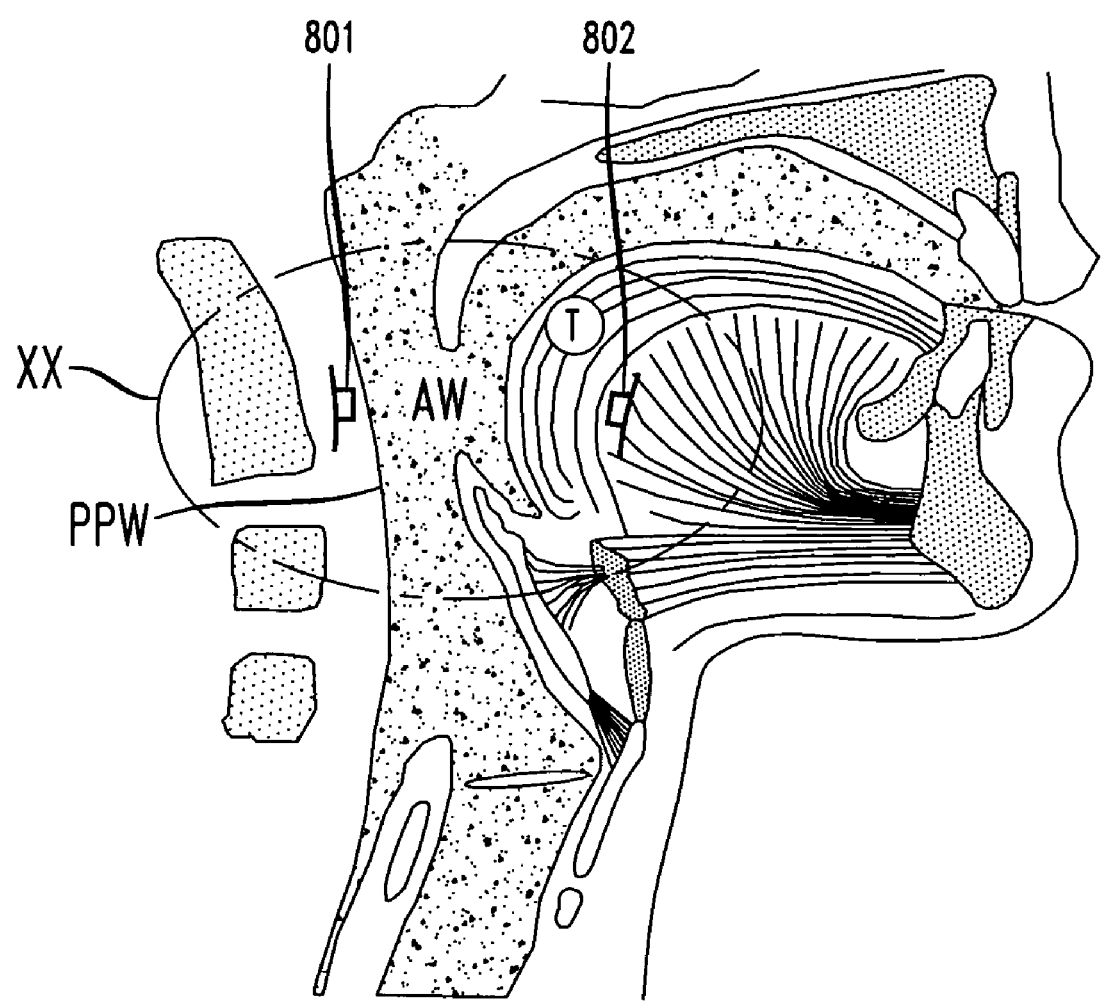
FIG. 8 is a cross-sectional view of a patient's airway showing implanted devices according to one embodiment of the invention.
Figure 9:
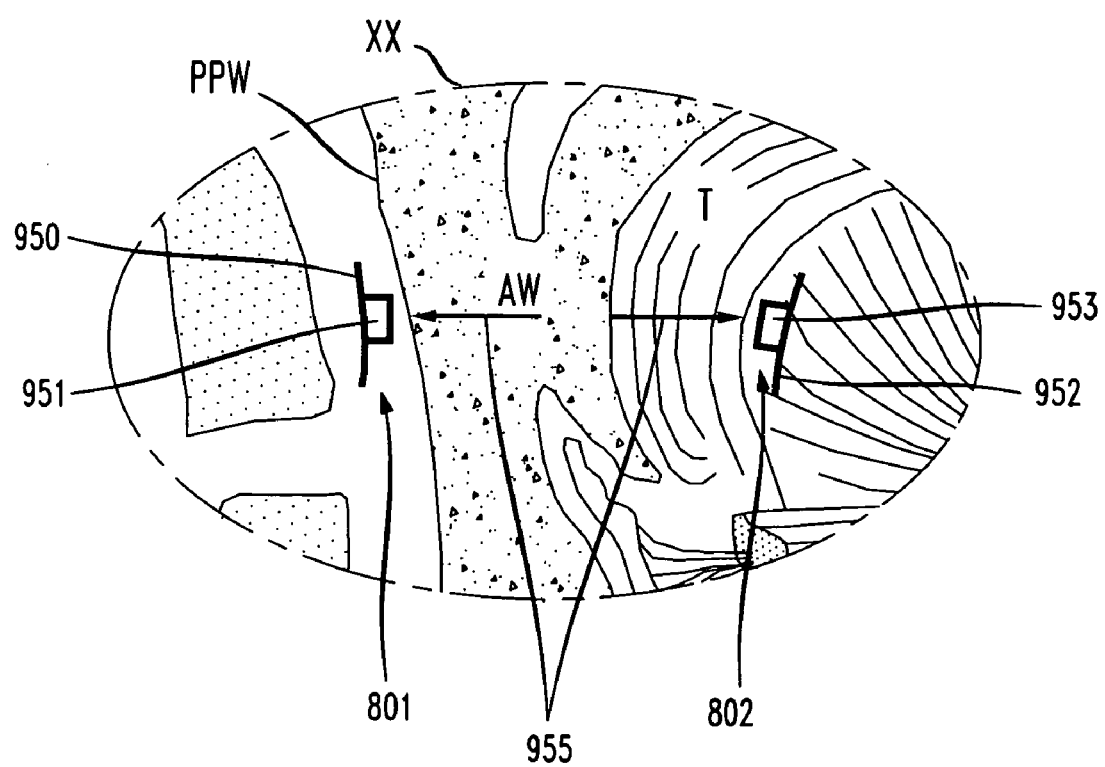
FIG. 9 is an enlargement of the region XX of FIG. 8.

An elliptical portion X-X of the cross sectional view of FIG. 8 is enlarged in the view shown in FIG. 9. The magnets 951, 953 are oriented so that like poles face each other, as shown in FIG. 7B. In that way, repelling forces 955 are exerted between the two magnets. Those forces are transmitted through each of the sheet-like elements 950, 952 into surrounding tissue, causing the soft tissue of the tongue T to be biased out of the airway AW and away from the posterior pharyngeal wall PPW. As the tongue approaches the posterior pharyngeal wall, as occurs in sleep apnea episodes of some patients, the repelling force between the two magnets increases, preventing or reducing the severity of a sleep apnea episode.

The sheet-like elements have sufficient flexibility to evenly distribute the magnetic force 955 to the surrounding tissue without any undue stress concentration. The magnetic attachment of each magnet 951, 953 to its sheet-like element 950, 952 is sufficiently strong to prevent migration or flipping of the magnets under the repelling force 955.

Each of the devices 801, 802 may initially be placed without additional securement, relying on the tissue engaging properties of the sheet-like elements 950, 952 to hold the devices in place. Alternatively, the devices may be initially secured to surrounding tissue using sutures that directly secure the sheet-like element 950 to tissue behind the posterior pharyngeal wall, and directly secure the sheet-like element 952 to tissue of the tongue. Over time, tissue ingrowth in and around the sheet-like elements permanently secures the devices to the surrounding tissues, enabling forces to be transmitted through the sheet-like elements into the surrounding tissue.

The implantable devices may be placed using a trocar in a minimally invasive approach. Alternatively, the devices of the invention may also be placed using an open, direct visualization approach to the pharynx from the side of a patient's neck, and a direct approach to the tongue through a patient's mouth. In addition to placement in the tongue and behind the posterior pharyngeal wall, devices of the invention may be effectively used in placements behind the lateral pharyngeal wall, and in other tissue in proximity with a patient's airway to maintain the airway in an open position.

One or both of the sheet-like elements 950, 952 may be initially implanted without the magnets 951, 953. In that way, healing and tissue ingrowth occurs in the absence of magnetic forces being exerted on the sheet-like elements, which may otherwise cause them to move in the surrounding tissue before tissue ingrowth occurs, discouraging healing. The magnets are subsequently added in a second procedure, after the sheet-like elements have been fully stabilized in the surrounding tissue during healing through tissue ingrowth. Because attachment of the magnets to the sheet-like elements is magnetic and involves simply placing the magnets on the sheet-like elements, the second procedure is simplified.

In use, it is sometimes necessary to change a magnet in situ in order to increase or decrease the force 955. In many cases, the correct treatment force can be known only after the devices are in place and operational. The devices of the present invention permit one or both of the magnets 951, 953 to be changed without reversing the tissue ingrowth and stabilization that has already taken place. The sheet-like element is only minimally disturbed in the surrounding tissue while removing a magnet by overcoming the magnetic forces holding it in place on the sheet-like element. A new magnet may then be installed.

Figure 10:
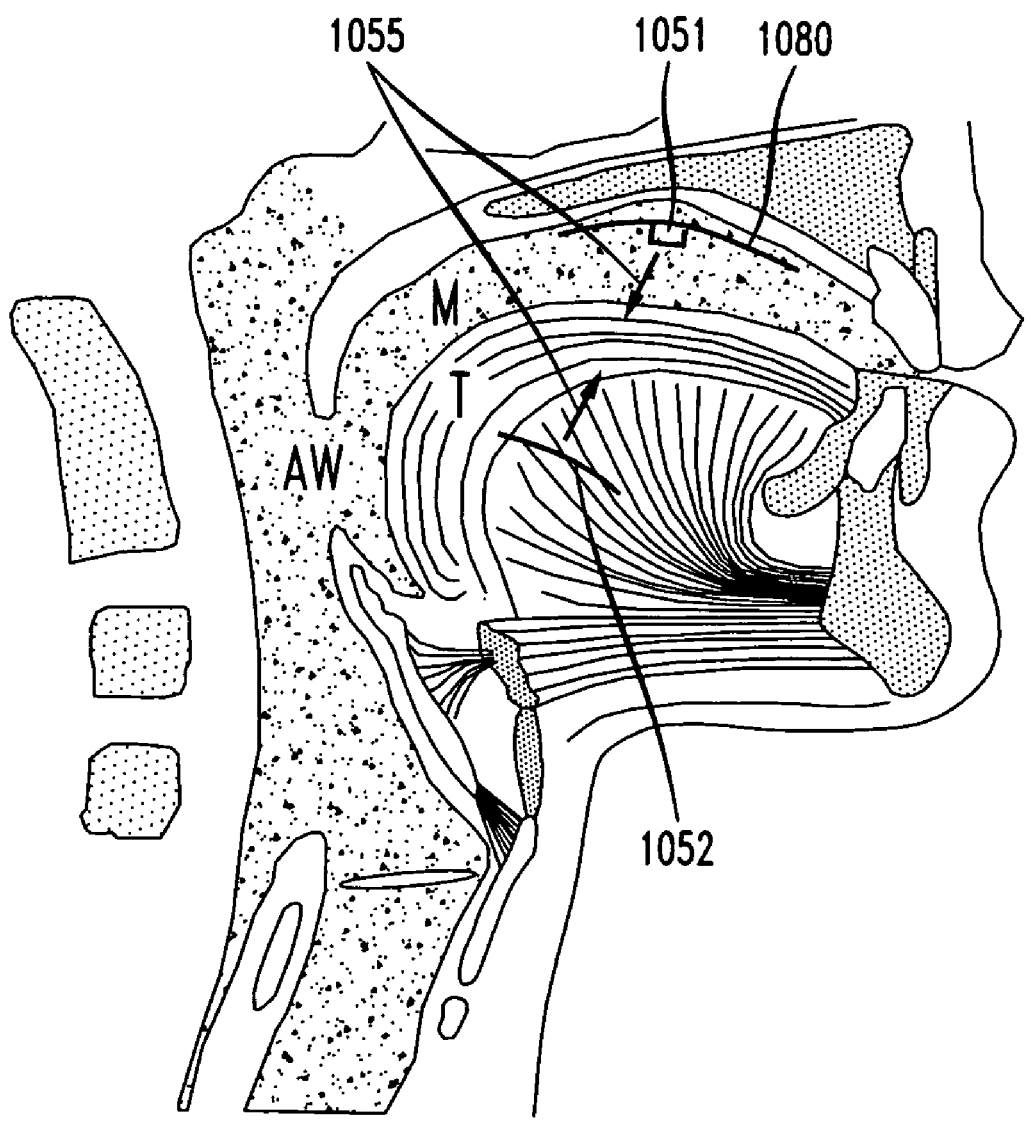
FIG. 10 is a cross-sectional view of a patient's airway showing an implanted device and appliance according to one embodiment of the invention.

Another configuration of the devices of the invention, shown in FIG. 10, utilizes an attractive force between a magnet 1051 and an implantable device 1052 comprising only a ferromagnetic sheet-like element that exerts attractive forces in the presence of a magnetic field. The device 1052 is implanted in the patient's tongue T. The tongue is allowed to heal and tissue ingrowth is permitted to fully stabilize the device in surrounding tissue prior to subjecting the device to magnetic forces.

The magnet 1051 is part of an appliance 1080 worn by the patient in the mouth M at night. The magnet 1051 exerts an attractive force on the implanted device 1052, forcing the tongue T in a direction away from the airway AW. In that way, sleep apnea episodes are reduced or eliminated.

The device 1052 has sufficient flexibility to evenly distribute the magnetic force 1055 to the surrounding tissue of the tongue T without any undue stress concentration. The device additionally has a compliance similar to that of the surrounding tissue to reside in the tongue T during the day without causing undue discomfort. While illustrated as an appliance to be worn in the mouth, the appliance 1080 may alternatively be worn externally in another area proximate the airway, such as the neck, chin or face.

Figure 11A:
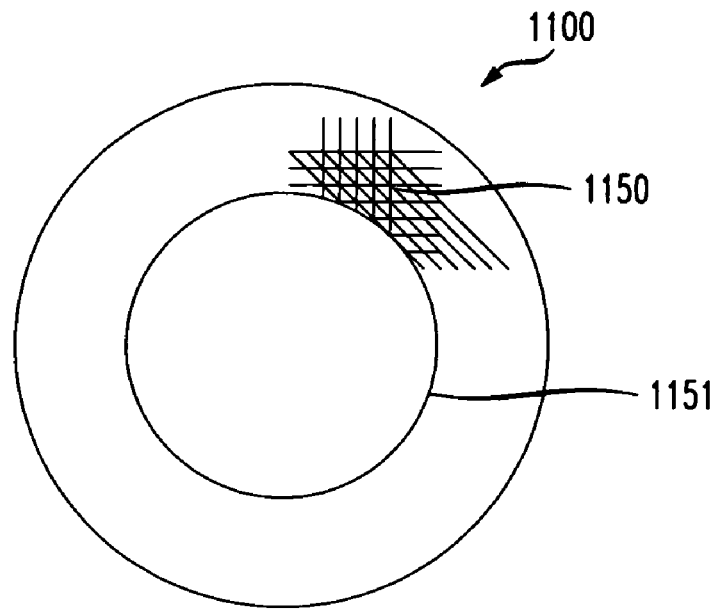
FIG. 11A is a schematic plan view of an implantable device including a magnetorheological material in accordance with one embodiment of the invention.
Figure 11B:
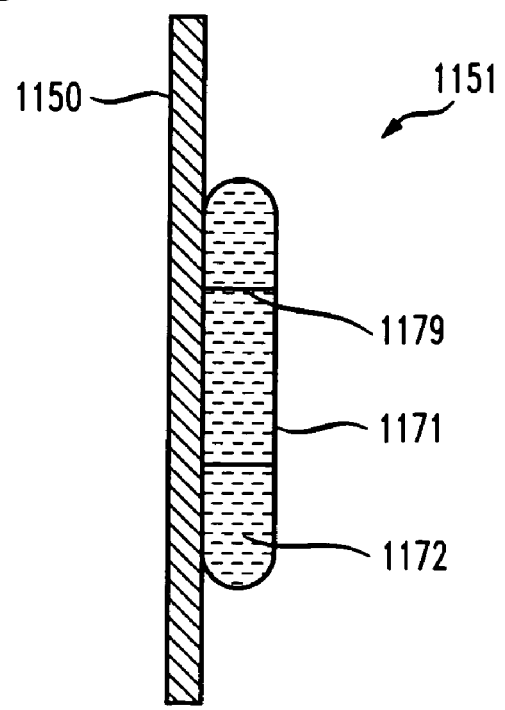
FIG. 11B is a schematic side view of the device of FIG. 11A.

Another device 1100 in accordance with the invention, shown in FIGS. 11A and FIG. 11B, comprises a sheet-like element 1150 for promoting tissue ingrowth. The sheet-like element 1150 may be circular as shown, or may be formed in another shape to better conform to surrounding tissue. The sheet-like element may be a medical textile, as shown, or may be a film, as described above. Attached to the sheet-like element is a magnetorheological system 1151 comprising a bladder 1171 containing a magnetorheological fluid 1172 (FIG. 11B). As is known in the art, magnetorheological fluid is a suspension of ferromagnetic particles in a gel or liquid carrier fluid. The suspension increases greatly in apparent viscosity or undergoes another physical change when subjected to a magnetic field. For example, the viscosity of the suspension may increase to the point where the fluid becomes a viscoelastic solid when subjected to a magnetic field.

The bladder 1171 may be constructed of a biocompatible polymer film such as nylon, polyester, polyurethane, silicone or polypropylene. The bladder must also be chemically compatible with the magnetorheological fluid 1172. In a preferred embodiment, the bladder 1171 maintains the magnetorheological fluid in a flattened, substantially planar shape, resisting localized thickening or bunching of the fluid. To that end, stays or battens 1179 may be attached to the inner walls of the bladder 1171.

The magnetorheological system 1151 is attached to the sheet-like element 1150 using a biocompatible adhesive, or by welding, encapsulating or any other connection technique that preserves the integrity of the bladder wall.

Figure 12:
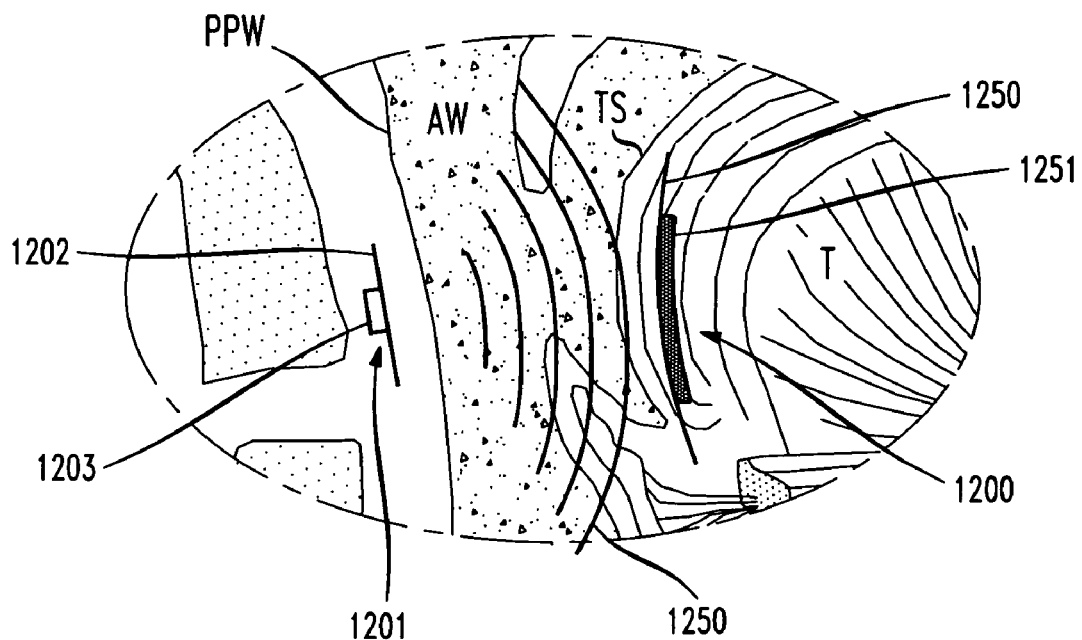
FIG. 12 is a cross-section of a patient's airway showing an implanted device in accordance with one embodiment of the invention.

The implantable magnetorheological device may be used in accordance with methods of the invention in treating sleep apnea, as shown in FIG. 12. A device 1200, including a sheet-like element 1250 and a magnetorheological system 1251, is deployed in the midline of the rear of the tongue T. An implantable magnetic device 1201, including a permanent magnet 1203 attached to a sheet-like element 1202, is placed in a posterior space created behind the posterior pharyngeal wall PPW.

During a sleep apnea event, the rear tongue surface TS may descend toward the posterior pharyngeal wall PPW, potentially blocking the airway AW. That movement of the rear of the tongue, however, brings the magnetorheological device 1200 into closer proximity with the magnetic device 1201, subjecting the magnetorheological fluid to an increased magnetic field 1250. The interaction of the magnetic field with the magnetorheological fluid stiffens the device 1200, resisting further decent of the rear of the tongue.

The response of a magnetorheological system in the magnetic field is highly dependent on the field strength, and can be finely adjusted by adjusting field strength. For that reason, it may become necessary or desirable to replace the magnet 1203 with another magnet having a different strength, and thereby adjust the system response to match the particular physiology of the patient. To that end, the sheet-like element 1202 may be a ferromagnetic sheet-like element as described above, and the magnet 1203 may be attached to the sheet-like element solely by magnetic attraction between the magnet and the sheet-like element. To adjust the system response, the magnet 1203 may be changed with minimum disturbance of the tissue ingrowth and stabilization that has already taken place. The magnet 1203 may be removed by overcoming the magnetic forces holding it in place on the sheet-like element 1202, and a new magnet may then be installed.

Figure 13:
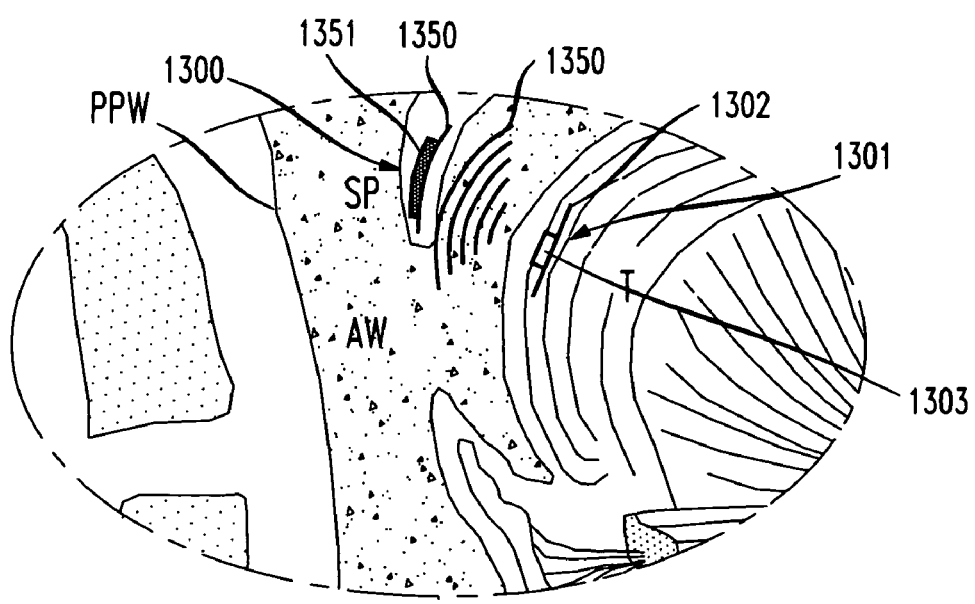
FIG. 13 is a cross-section of a patient's airway showing an implanted device in accordance with another embodiment of the invention.

The implantable magnetorheological device may alternatively be used in accordance with methods of the invention in controlling snoring, as shown, for example, in FIG. 13. A device 1300, including a sheet-like element 1350 and a magnetorheological system 1351, is implanted within the soft palate SP, with the substantially planar surfaces of the magnetorheological system 1351 extending substantially parallel to the surfaces of the soft palate. An implantable magnetic device 1301, including a permanent magnet 1303 attached to a sheet-like element 1302, is implanted in the rear of the tongue T.

In many cases, snoring is caused as the tongue T approaches the soft palate SP, or as the soft palate collapses against the posterior pharyngeal wall PPW. By placing the magnetorheological system 1300 within the soft palate, that tissue is selectively stiffened as it approaches the implantable magnetic device 1301. In the embodiment shown in FIG. 13, the soft palate SP is stiffened as the rear surface of the tongue T approaches the soft palate. Alternatively, the implantable magnetic device 1301 may be placed in a posterior space created behind the posterior pharyngeal wall PPW, as shown in FIG. 12. In either case, movement within the oropharyngeal area typically associated with snoring brings the magnetorheological device 1300 into proximity with the implantable magnetic device 1301, subjecting the magnetorheological fluid to an increased magnetic field 1350. The interaction of the magnetic field with the magnetorheological fluid stiffens the magnetorheological system 1351, resisting vibration and fluttering of the soft palate that is associated with snoring.

As described above with reference to FIG. 12, the magnet 1303 may be attached to the sheet-like element 1302 solely by magnetic attraction between the magnet and the sheet-like element. To adjust the response of the magnetorheological device 1300, the magnet 1303 may be changed with minimum disturbance of the tissue ingrowth and stabilization that has already taken place around the sheet-like element 1302. The magnet 1303 may be removed by overcoming the magnetic forces holding it in place on the sheet-like element 1302, and a new magnet may then be installed.

The devices, systems and surgical methods described above provide simple, minimally invasive procedures that may potentially be performed on an outpatient basis. Results of the procedures are both immediate and long-term. The implanted devices do not impact the hyoid bone or soft palate, and are therefore less likely to affect swallowing or speech. The invention furthermore uses materials with a long-term history of biocompatibility.

The foregoing Detailed Description and accompanying figures are to be understood as being in every respect illustrative and exemplary, but not restrictive, and the scope of the invention disclosed herein is not to be determined from the Description of the Invention, but rather from the Claims as interpreted according to the full breadth permitted by the patent laws. For example, while the implantable devices of the invention have been illustrated in certain exemplary configurations in the head and neck, other magnetic configurations and other target tissues are contemplated. It is to be understood that the embodiments shown and described herein are only illustrative of the principles of the present invention and that various modifications may be implemented by those skilled in the art without departing from the scope and spirit of the invention.

What is claimed is:

1. A method for surgically treating obstructive sleep apnea, the method comprising:
   delivering an implantable device into a soft tissue component of a human air passage, the implantable device comprising a textile including multiple ferromagnetic filaments forming tissue ingrowth features;
   subjecting the implantable device to a first magnetic field so as to exert a force on the implantable device; and
   attaching a permanent magnet to the implantable device to create a second magnetic field associated with the implantable device, the permanent magnet being attached solely by magnetic interaction between the permanent magnet and the implantable device.

2. The method of claim 1, further comprising:
   adjusting the second magnetic field by replacing the permanent magnet with a second permanent magnet, the second permanent magnet being attached solely by magnetic interaction between the second permanent magnet and the implantable device.

3. The method of claim 1, further comprising:
   delivering an implant including a second permanent magnet into tissue in a vicinity of the soft tissue component of the human air passage, whereby the second permanent magnet creates the first magnetic field.

4. The method of claim 1, further comprising:
   providing a second permanent magnet adapted to be used externally or in the mouth, whereby the second permanent magnet creates the first magnetic field.

5. The method of claim 1, wherein the ferromagnetic filaments are drawn from a ferromagnetic material.

6. The method of claim 1, wherein the implantable device comprises a woven element formed from the multiple ferromagnetic filaments.

7. The method of claim 1, wherein the implantable device comprises a knitted element formed from the multiple ferromagnetic filaments.

8. A method for surgically treating obstructive sleep apnea, the method comprising:
   delivering an implantable device into a soft tissue component of a human air passage, the implantable device comprising a textile including multiple ferromagnetic filaments forming tissue ingrowth features;
   attaching a permanent magnet to the implantable device to create a magnetic field associated with the implantable device, the permanent magnet being attached solely by magnetic interaction between the permanent magnet and the implantable device; and
   adjusting the magnetic field by replacing the permanent magnet with a second permanent magnet by removing the permanent magnet by overcoming attractive forces between the permanent magnet and the implantable device and attaching the second permanent magnet solely by magnetic interaction between the second permanent magnet and the implantable device.

9. The method of claim 8, further comprising:
   delivering a third permanent magnet into tissue in a vicinity of the soft tissue component of the human air passage, whereby the third permanent magnet exerts a force on the implantable device.

10. The method of claim 8, further comprising:
    providing a third permanent magnet adapted to be used externally or in the mouth, whereby the third permanent magnet exerts a force on the implantable device.

11. The method of claim 8, wherein the implantable device is a sheet-like element.

* * * * *